United States Patent
Batista

(10) Patent No.: US 12,310,422 B2
(45) Date of Patent: May 27, 2025

(54) INHALER MOUTHPIECE WITH SEPARATE FLAVOUR AIR CHANNEL

(71) Applicant: PHILIP MORRIS PRODUCTS S.A., Neuchâtel (CH)

(72) Inventor: Rui Nuno Batista, Morges (CH)

(73) Assignee: Philip Morris Products S.A., Neuchatel (CH)

( * ) Notice: Subject to any disclaimer, the term of this patent is extended or adjusted under 35 U.S.C. 154(b) by 468 days.

(21) Appl. No.: 17/801,859

(22) PCT Filed: Feb. 23, 2021

(86) PCT No.: PCT/IB2021/051524
§ 371 (c)(1),
(2) Date: Aug. 24, 2022

(87) PCT Pub. No.: WO2021/171182
PCT Pub. Date: Sep. 2, 2021

(65) Prior Publication Data
US 2023/0092745 A1 Mar. 23, 2023

(30) Foreign Application Priority Data
Feb. 26, 2020 (EP) .................................... 20159619

(51) Int. Cl.
*A24F 42/60* (2020.01)
*A24F 7/00* (2006.01)
(Continued)

(52) U.S. Cl.
CPC ................ *A24F 42/60* (2020.01); *A24F 7/00* (2013.01); *A24F 42/20* (2020.01);
(Continued)

(58) Field of Classification Search
CPC ............ A24F 42/60; A24F 7/00; A24F 42/20; A61M 15/0025; A61M 15/003
See application file for complete search history.

(56) References Cited

U.S. PATENT DOCUMENTS

| | | |
|---|---|---|
| 9,554,595 B2 | 1/2017 | Buchberger |
| 9,993,601 B2 | 6/2018 | Jung et al. |

(Continued)

FOREIGN PATENT DOCUMENTS

| | | |
|---|---|---|
| CA | 3033621 | 3/2018 |
| EP | 2544744 | 1/2013 |

(Continued)

OTHER PUBLICATIONS

EP Search Report for EP 20159619.4 issued by the European Patent Office on Sep. 11, 2020; 5 pgs.

(Continued)

*Primary Examiner* — Christopher M Rodd
*Assistant Examiner* — Jennifer A Kessie
(74) *Attorney, Agent, or Firm* — Mueting Raasch Group

(57) ABSTRACT

An inhaler article includes a body extending along a longitudinal axis from a mouthpiece end to a distal end. A capsule cavity may be within the body bounded downstream by a mouthpiece. An air inlet at the distal end and an air outlet at the mouthpiece end. A first mouthpiece air channel may extend from the distal air inlet, through the capsule cavity to the mouthpiece air outlet. A second mouthpiece air channel may extend from a point downstream of the separator to the mouthpiece air outlet. The second mouthpiece air channel may be separate from the first mouthpiece air channel. A coating layer of flavour may be disposed on a surface of the second mouthpiece air channel and a protective layer may be disposed on the coating layer of flavour.

20 Claims, 4 Drawing Sheets

(51) Int. Cl.
*A24F 42/20* (2020.01)
*A61M 15/00* (2006.01)
*A61M 15/06* (2006.01)

(52) U.S. Cl.
CPC ....... *A61M 15/0025* (2014.02); *A61M 15/003* (2014.02); *A61M 15/06* (2013.01); *A61M 2202/064* (2013.01)

(56) References Cited

U.S. PATENT DOCUMENTS

| | | |
|---|---|---|
| 11,033,692 B2 | 6/2021 | Stenzler et al. |
| 2014/0083423 A1* | 3/2014 | Jung ................ A61M 15/0005 128/203.12 |
| 2018/0228216 A1* | 8/2018 | Saygili ................ A61M 11/042 |

FOREIGN PATENT DOCUMENTS

| | | |
|---|---|---|
| GB | 2461008 | 12/2009 |
| WO | 20140110119 | 7/2014 |
| WO | 20170109626 | 6/2017 |

OTHER PUBLICATIONS

Cohen et al., "GRAS Flavoring Substances," 27. GRAS Flavoring Substances. Food Technology for Flavoring Extract Manufacturers Association, Aug. 2015:69(8):40-59.
Hall, R.L. & Oser, B.L., "Recent Progress in the Consideration of Flavoring Ingredients under the Food Additive Amendments 3. GRAS substances," Food Technology, Feb. 1965: p. 151-197.
International Search Report and Written Opinion for PCT/IB2021/051524, issued by the European Patent Office on Apr. 9, 2021; 12 pgs.

\* cited by examiner

INHALER MOUTHPIECE WITH SEPARATE FLAVOUR AIR CHANNEL

This application is the § 371 U.S. National Stage of International Application No. PCT/IB2021/051524, filed 23 Feb. 2021, which claims the benefit of European Application No. 20159619.4, filed 26 Feb. 2020, the disclosures of which are incorporated herein by reference.

This disclosure relates to an inhaler article including a mouthpiece with a separate flavour air channel. The inhaler article may be a dry powder inhaler where the flavour element is exposed to an air flow channel that is isolated from the dry powder air flow channel within the inhaler.

Dry powder inhalers are not always fully suitable to provide dry powder particles to the lungs at inhalation or air flow rates that are within conventional smoking regime inhalation or air flow rates. Dry powder inhalers may be complex to operate or may involve moving parts. Dry powder inhalers often strive to provide an entire dry powder dose or capsule load in a single breath.

Flavour may be desired for consumption of inhalable dry powders. To achieve this, flavour particles may be combined with the dry powder materials. Flavour particles may not be compatible with the dry powder materials. Flavour particles that are combined with the dry powder may degrade or agglomerate the dry powder.

It would be desirable to provide an inhaler having a flavour element that is separated from the dry powder capsule or receptacle. It would be desirable to provide an inhaler where the flavour element is disposed in the mouthpiece. It would be desirable to provide an inhaler having a flavor element that is exposed to an air flow path. It would be desirable to provide an inhaler having a dry powder air flow path. And, it would be desirable to provide an inhaler having a flavor element in an air flow path that is isolated from the dry powder air flow. It would be desirable to provide an inhaler to allow release of flavour on demand by the consumer. It would be desirable to provide a sealed inhaler that may be assembled at high speed. It would be desirable to provide an inhaler that has a flavour element that is interchangeable with a different flavour element. It would be desirable to provide an inhaler article that has a form that is easy to hold and familiar to a user, similar to a conventional cigarette. It would be desirable to provide an inhaler where the user easily activates the flavour element.

According to an aspect of the present invention, there is provided an inhaler article including a body extending along a longitudinal axis from a mouthpiece end to a distal end. A capsule cavity may be within the body bounded downstream by a mouthpiece. The inhaler may have an air inlet at the distal end and an air outlet at the mouthpiece end. A separator may be between the capsule cavity and the mouthpiece to contain the capsule within the capsule cavity, including at least one aperture to form an air flow path through the capsule cavity to the mouthpiece. A first mouthpiece air channel may extend from the distal air inlet, through the capsule cavity to the mouthpiece air outlet. A second mouthpiece air channel may extend from a point downstream of the separator to the mouthpiece air outlet. The second mouthpiece air channel may be separate from the first mouthpiece air channel. A coating layer of flavour may be disposed on a surface of the second mouthpiece air channel and a protective layer may be disposed on the coating layer of flavour.

The inhaler article separates or isolates the flavour element from the dry powder capsule or receptacle, this may improve or enhance the stability of the dry powder contained within the dry powder capsule or receptacle. The protective layer may be in contact with the flavour element and releasably adhere to the coating layer of flavour. Advantageously, the user may easily activate or expose the coating layer of flavour by removing the protective layer from the inhaler.

The inhaler article may include a coating layer of flavour defining at least a portion of the second mouthpiece air channel.

The inhaler article may include the second mouthpiece air channel having an air inlet that extends though the body of the inhaler. The second mouthpiece air channel having an air inlet though the body or sidewall of the inhaler article provides a separate air inlet that does not contain dry powder particles from the capsule cavity.

The inhaler article may include the second mouthpiece air channel having an air inlet that extends though the mouthpiece. The second mouthpiece air channel having an air inlet though the mouthpiece or sidewall of the mouthpiece ensures a separate air inlet that does not contain dry powder particles from the capsule cavity.

The inhaler article may include the coating layer of flavour forming a gel layer. Providing the coating layer of flavour in gel form may stabilize the flavour and be a convenient deposition technique during assembly. Providing the coating layer of flavour in gel form may allow for a tailored controlled release of flavour during consumption.

The inhaler article may include the coating layer of flavour contacts an inner diameter of the mouthpiece.

The inhaler article may include the protective layer adhering to the coating layer of flavour and the protective layer defining a coaxial cylinder with the body longitudinal axis. Providing the coating layer of flavour and protective layer in this manner enables a simplified construction and high-speed assembly.

The inhaler article may include the protective layer comprising foil, paper, polymer, or combinations thereof.

The mouthpiece may fit over the body of the inhaler. The body of the inhaler may be shaped to accommodate the mouthpiece. For example, the body of the inhaler may have a mouthpiece region having a reduced diameter, structured and arranged to fit inside the mouthpiece. The mouthpiece region of the inhaler body and the mouthpiece may form coaxial cylinders.

In embodiments, the second air channel is formed between the internal surface of the mouthpiece and an external surface of the narrowed portion of the mouthpiece end of the body of the inhaler. The coating layer of flavour may be disposed on an inner surface of the mouthpiece.

The mouthpiece can be removed and exchanged with another mouthpiece by removing the mouthpiece from narrowed mouthpiece end of the body of the inhaler using a sliding motion and sliding on a new mouthpiece. This may be useful to replace a depleted flavour element or change the type of flavour element as described by the user.

The inhaler article may further include a mouthpiece endcap sealing the mouthpiece air outlet. The mouthpiece endcap may be configured to be removable from the mouthpiece element to expose the mouthpiece air outlet. The mouthpiece endcap may advantageously seal the mouthpiece end of the inhaler to provide an enhanced shelf life of the inhaler and associated powder.

The inhaler article may include the protective layer fixed to the mouthpiece endcap and configured to be removed from the mouthpiece element with the mouthpiece endcap. Attaching the protective layer to the mouthpiece endcap provides a convenient removal action by the user.

In addition, the protective layer fixed to the mouthpiece endcap may cover the air inlet of the second air channel before the protective layer is removed by the user. This prevents air from interacting with the coating layer of flavour before the device is activated by the user.

The inhaler article may include the protective layer defining a spiral configuration when removed from the mouthpiece element. Advantageously this spiral configuration allows for easy removal of the protective layer without damaging the coating layer of flavour.

The inhaler article may further include a circumferential line of weakness forming an interface between the mouthpiece endcap and the mouthpiece end. Advantageously this circumferential line of weakness provides for a reliable and clean separation interface of the mouthpiece end cap from the inhaler body or mouthpiece body.

The inhaler article may include the mouthpiece endcap having an outer diameter equal to an outer diameter of the inhaler article body, and the mouthpiece endcap being coaxial with the inhaler article body.

The inhaler article may further include a capsule disposed within the capsule cavity. The capsule may contain pharmaceutically active particles including nicotine. The pharmaceutically active particles may have a mass median aerodynamic diameter of about 5 micrometres or less, or in a range from about 0.5 micrometres to about 4 micrometres, or in a range from about 1 micrometre to about 3 micrometres.

The inhaler article may include the first mouthpiece air channel being coaxial with the second mouthpiece air channel. The first mouthpiece air channel and the second mouthpiece air channel may be coaxial with the longitudinal axis of the inhaler article body.

The inhaler article may include the mouthpiece may be removable and interchangeable to allow for the user to select or change the type of coating layer of flavour.

Advantageously, this inhaler article minimizes moving parts. Advantageously, the inhaler article efficiently provides nicotine particles to the lungs at inhalation or air flow rates that are within conventional smoking regime inhalation or air flow rates. The inhaler delivers the nicotine powder with an inhaler article that has a form similar to a conventional cigarette. The inhaler article described herein may provide a dry powder to the lungs at inhalation or air flow rates that are within conventional smoking regime inhalation or air flow rates. A consumer may take a plurality of inhalations or "puffs" where each "puff" delivers a fractional amount of dry powder contained within a capsule contained within the capsule cavity. This inhaler article may have a form similar to a conventional cigarette and may mimic conventional smoking. This inhaler article may be simple to manufacture and convenient to use by a consumer.

Air flow management through a capsule cavity of the inhaler article may cause a capsule, that may be contained therein to rotate during inhalation and consumption. The capsule may contain particles containing nicotine (also referred to as "nicotine powder" or "nicotine particles"). Rotation of the pierced capsule may suspend and aerosolize the nicotine particles released from the pierced capsule into the inhalation air moving through the inhaler article. The particles containing nicotine may pass through a first mouthpiece air channel that is separate or isolated from the flavour element as flavour particles are released from the coating layer of flavour into the second mouthpiece air channel. The flavour particles may be larger than the nicotine particles and may assist in transporting the nicotine particles into the lungs of the user while the flavour particles preferentially remain in the mouth or buccal cavity of the user. The nicotine particles and flavor particles may be delivered with the inhaler article at inhalation or air flow rates that are within conventional smoking regime inhalation or air flow rates.

The term "gel" refers to a substantially dilute cross-linked system, which exhibits no flow when in the steady state. By weight, gels are mostly liquid, yet they behave like solids due to a three-dimensional cross-linked network within the liquid. It is the crosslinking within the fluid that gives a gel its structure (hardness) and contributes to the adhesive stick (tack). In this way, gels are a dispersion of molecules of a liquid within a solid medium.

The term "nicotine" refers to nicotine and nicotine derivatives such as free-base nicotine, nicotine salts and the like.

The term "flavourant" or "flavour" refers to organoleptic compounds, compositions, or materials that alter and are intended to alter the taste or aroma characteristics of nicotine during consumption or inhalation thereof.

The terms "upstream" and "downstream" refer to relative positions of elements of the inhaler article described in relation to the direction of inhalation air flow as it is drawn through the inhaler article.

The terms "proximal" and "distal" are used to describe the relative positions of components, or portions of components, of the inhaler article. Inhaler articles, according to the present invention have a proximal end. In use, the nicotine particles exit the proximal end of the inhaler article for delivery to a user. The inhaler article has a distal end opposing the proximal end. The proximal end of the inhaler article may also be referred to as the mouth end or mouthpiece end.

All scientific and technical terms used herein have meanings commonly used in the art unless otherwise specified. The definitions provided herein are to facilitate understanding of certain terms used frequently herein.

As used herein, the singular forms "a", "an", and "the" encompass embodiments having plural referents, unless the content clearly dictates otherwise.

As used herein, "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open-ended sense, and generally mean "including, but not limited to". It will be understood that "consisting essentially of", "consisting of", and the like are subsumed in "comprising," and the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the disclosure, including the claims.

This disclosure relates to an inhaler article including a mouthpiece with a separate flavour air channel. The inhaler article may be a dry powder inhaler where the flavour element is isolated from the dry powder air flow within the inhaler. The inhaler article may be configured to initiate swirling or rotational inhalation airflow during consumption.

An inhaler article includes a body extending along a longitudinal axis from a mouthpiece end to a distal end. A capsule cavity may be within the body bounded downstream by a mouthpiece. An air inlet at the distal end and an air outlet at the mouthpiece end. A separator may be between the capsule cavity and the mouthpiece including at least one aperture to form an air flow path from the capsule cavity to the mouthpiece. A first mouthpiece air channel may extend from the distal air inlet, through the capsule cavity to the mouthpiece air outlet. A second mouthpiece air channel may extend from a point downstream of the separator to the mouthpiece air outlet. The second mouthpiece air channel may be separate from the first mouthpiece air channel. A coating layer of flavour may be disposed on a surface of the second mouthpiece air channel and a protective layer may be disposed on the coating layer of flavour.

Isolating or separating the first mouthpiece air channel from the second mouthpiece air channel prevents air flow from the capsule cavity from flowing through the second mouthpiece air channel. This may be useful if the dry powder particles adhere to or degrade the coating layer of flavour.

Preferably the first mouthpiece air channel is coaxial with the second mouthpiece air channel. Preferably the first mouthpiece air channel is coaxial and parallel with the second mouthpiece air channel. The first mouthpiece air channel and the second mouthpiece air channel may be coaxial with the longitudinal axis of the inhaler article body.

The second mouthpiece air channel may be formed by disposing the mouthpiece about a reduced diameter portion of the inhaler body. The shaped, educed diameter, or narrowed portion of the body may extend along the mouthpiece region to the mouthpiece end of the inhaler article. The mouthpiece may fit over the reduced diameter portion of the inhaler body to form the second mouthpiece air channel.

The second mouthpiece air channel may define an annular void space between the mouthpiece inner surface and the external surface of the reduced diameter portion of the inhaler body. The coating layer of flavour may be disposed on the mouthpiece inner surface. The coating layer of flavour may cover about 50% or more of the mouthpiece inner surface. The coating layer of flavour may cover about 75% or more of the mouthpiece inner surface. The coating layer of flavour may cover about 90% or more of the mouthpiece inner surface.

The mouthpiece may be a replaceable element on the inhaler body. Thus a user may remove a mouthpiece having a depleted coating layer of flavour and place a different or refreshed mouthpiece onto the inhaler body.

The inhaler article may include a coating layer of flavour defining at least a portion of the second mouthpiece air channel. The coating layer of flavour may have a uniform thickness about the circumference of the mouthpiece second air channel. The coating layer of flavour may have a thickness in a range from about 5 micrometers to about 60 micrometers, preferably from about 10 micrometers to about 50 micrometers, most preferably from about 15 micrometers to about 35 micrometers The coating layer of flavour may have a longitudinal length that may be coextensive with the mouthpiece second air channel. The coating layer of flavour may have a longitudinal length in a range from about 5 millimetres to about 25 millimetres, preferably from about 7 millimetres to about 20 millimetres, most preferably from about 9 millimetres to about 18 millimetres The inhaler article may include the second mouthpiece air channel having an air inlet that extends though the body of the inhaler. The second mouthpiece air channel having an air inlet though the body or sidewall of the inhaler article ensures a separate air inlet that does not contain dry powder particles from the capsule cavity. The air inlet for the second mouthpiece air channel may be defined by a series of apertures or holes through the body or sidewall of the inhaler article. The series of apertures or holes through the body or sidewall of the inhaler article may extend circumferentially about the body or sidewall of the inhaler article.

The inhaler article may include the second mouthpiece air channel having an air inlet that extends though and along a length of the mouthpiece. The second mouthpiece air channel having an air inlet though the mouthpiece or sidewall of the mouthpiece ensures a separate air inlet that does not contain dry powder particles from the capsule cavity.

The mouthpiece may be removable and interchangeable to allow for the user to select or change the type of coating layer of flavour.

The inhaler article may include the coating layer of flavour forming a gel layer. Providing the coating layer of flavour in gel form may stabilize the flavour and be a convenient deposition technique during assembly. Providing the coating layer of flavour in gel form may allow for a tailored controlled release of flavour during consumption.

The inhaler article may include the coating layer of flavour disposed between the protective layer and a mouthpiece inner surface. The coating layer of flavour may contact the mouthpiece inner surface and be adhered to the mouthpiece inner surface.

The inhaler article may include the coating layer of flavour being a gel, or an oil or powder that is stabilized to form the coating layer of flavour.

The inhaler article may preferably include the coating layer of flavour forming a gel layer. Providing the coating layer of flavour in gel form may stabilize the flavour and be a convenient deposition technique during assembly. Providing the coating layer of flavour in gel form may allow for a tailored controlled release of flavour during consumption.

The inhaler article may include the coating layer of flavour defining an open cylinder. The open cylinder may be coaxial with the inner surface of the mouthpiece or an inner surface of the second mouthpiece air channel. The coating layer of flavour defining an open cylinder may have a uniform thickness about the circumference of the mouthpiece inner diameter. The coating layer of flavour may have a thickness in a range from about 5 micrometers to about 60 micrometers, preferably from about 10 micrometers to about 50 micrometers, most preferably from about 15 micrometers to about 35 micrometers. The coating layer of flavour defining an open cylinder may have a longitudinal length that may be coextensive with the second mouthpiece air channel. The coating layer of flavour may have a longitudinal length in a range from about 5 millimetres to about 25 millimetres, preferably from about 7 millimetres to about 20 millimetres, most preferably from about 9 millimetres to about 18 millimetres The coating layer of flavour includes one or more flavourants. The term "flavourant" or "flavour" refers to organoleptic compounds, compositions, or materials that alter and are intended to alter the taste or aroma characteristics of a pharmaceutically active or nicotine component during consumption or inhalation thereof. The term "flavourant" or "flavour" preferably refers to compounds disclosed in the Flavor & Extract Manufacturers Association (FEMA) Flavor Ingredient Library and in particular in the GRAS Flavoring Substances publications 3 to 27, for example, see Hall, R. L. & Oser, B. L., Food Technology, February 1965 pg. 151-197, and in the GRAS flavoring substances 27 S. M. Cohen et al., Food Technology August 2015 pg. 40-59, and intervening GRAS Flavoring Substances publications 4 to 26.

Flavourants or flavours refer to a variety of flavour materials of natural or synthetic origin. They include single compounds and mixtures. The flavour or flavourant has flavour properties that may enhance the experience of the pharmaceutically active or nicotine component during consumption. The flavour may be chosen to provide an experience similar to that resulting from smoking a combustible smoking article. For example, the flavour or flavourant may enhance flavour properties such as mouth fullness and complexity. Complexity is generally known as the overall balance of the flavour being richer without dominating single sensory attributes. Mouth fullness is described as perception of richness and volume in the mouth and throat of the consumer.

Suitable flavours include, but are not limited to, any natural or synthetic flavour, such as tobacco, smoke, menthol, mint (such as peppermint and spearmint), chocolate, licorice, citrus and other fruit flavours, gamma octalactone, vanillin, ethyl vanillin, breath freshener flavours, spice flavours such as cinnamon, methyl salicylate, linalool, bergamot oil, geranium oil, lemon oil, and ginger oil, and the like.

Other suitable flavours may include flavour compounds selected from the group consisting of an acid, an alcohol, an ester, an aldehyde, a ketone, a pyrazine, combinations or blends thereof and the like. Suitable flavour compounds may be selected, for example, from the group consisting of phenylacetic acid, solanone, megastigmatrienone, 2-heptanone, benzylalcohol, cis-3-hexenyl acetate, valeric acid, valeric aldehyde, ester, terpene, sesquiterpene, nootkatone, maltol, damascenone, pyrazine, lactone, anethole, iso-s valeric acid, combinations thereof, and the like.

Further specific examples of flavours may be found in the current literature, and are well-known to the person skilled in the art of flavouring, i.e. of imparting an odor or taste to a product.

The flavourant may be a high potency flavourant and may be used and detected at levels that would result in less than 200 parts per million in inhalation air flow. Examples of such flavourants are key tobacco aroma compounds such as beta-damascenone, 2-ethyl-3,5-dimethylpyrazine, phenylacetaldehyde, guaiacol, and furaneol. Other flavourants may only be sensed by humans at higher concentration levels. These flavourants, which are referred to herein as the lower potency flavourants, are typically used at levels that results in orders of magnitude higher amounts of flavourant released into the inhalation air. Suitable lower potency flavourants include, but are not limited to, natural or synthetic menthol, peppermint, spearmint, coffee, tea, spices (such as cinnamon, clove and ginger), cocoa, vanilla, fruit flavours, chocolate, eucalyptus, geranium, eugenol and linalool.

The inhaler article may include the protective layer adhering to the coating layer of flavour and the protective layer defining a coaxial cylinder with the body longitudinal axis. The protective layer preferably covers an entire coating layer of flavour surface. The protective layer may provide a moisture barrier for the coating layer of flavour. The protective layer may prevent flavour from migrating away from the coating layer of flavour.

The inhaler article may include the protective layer comprising foil, paper, polymer, or combinations thereof. The inhaler article may include the protective layer comprising a metal foil. Preferably the metal foil may be an aluminum foil. The metal foil may combine with a paper layer or polymeric layer to form a laminate protective layer.

The inhaler article protective layer may comprise polystyrol, polythiophene, polyethylene terephthalate, polyvinyl chlorides, or orientated polyamides.

The inhaler article protective layer may have a thickness in a range from about 20 micrometres to about 60 micrometers, or in a range from about 25 micrometres to about 40 micrometers, or in a range from about 25 micrometres to about 35 micrometers.

The inhaler article may further include a mouthpiece endcap sealing the mouthpiece air outlet. The mouthpiece endcap may be configured to be removable from the mouthpiece element to expose the mouthpiece air outlet. The mouthpiece endcap may advantageously seal the mouthpiece end of the inhaler to provide an enhanced shelf life of the inhaler and associated powder.

The inhaler article may include the protective layer fixed to the mouthpiece endcap and configured to be removed from the mouthpiece element with the mouthpiece endcap. Attaching the protective layer to the mouthpiece endcap provides a convenient removal action by the user.

The inhaler article may include the protective layer having a spiral or helical scoring line or spiral or helical line of weakness along a length of the protective layer. The spiral or helical scoring line or spiral or helical line of weakness may provide for the removal of the protective layer in a spiral configuration. This may aid in the removal of the protective layer from the mouthpiece.

The inhaler article may include the protective layer defining a spiral configuration when removed from the mouthpiece element. Advantageously this spiral configuration allows for easy removal of the protective layer without damaging the coating layer of flavour.

The inhaler article may further include a circumferential line of weakness forming an interface between the mouthpiece endcap and the mouthpiece end. Advantageously this circumferential line of weakness provides for a reliable and clean separation interface of the mouthpiece end cap from the inhaler body or mouthpiece body.

Once the protective layer is removed from the coating layer of flavour, flavour compounds volatize from the coating layer of flavour and combine with the particles comprising nicotine fluidized in the inhalation airflow.

The inhaler article may include the mouthpiece endcap having an outer diameter equal to an outer diameter of the inhaler article body, and the mouthpiece endcap being coaxial with the inhaler article body.

The inhaler body may resemble a smoking article or cigarette in size and shape. The inhaler body may have an elongated body extending along the longitudinal axis of the inhaler article. The inhaler body may have a substantially uniform outer diameter along the length of the elongated body. The inhaler body may have a circular cross-section that may be uniform along the length of the elongated body. The inhaler body may have an outer diameter in a range from about 6 mm to about 10 mm, or from about 7 mm to about 10 mm, or about 7 mm to about 9 mm, or about 7 mm to about 8 mm or about 7.2 mm. The inhaler body may have a length (along the longitudinal axis) in a range from about 40 mm to about 80 mm, or from about 40 mm to about 70 mm, or about 40 mm to about 50 mm, or about 45 mm.

The mouthpiece element located downstream of the capsule cavity may extend from the capsule cavity to the mouthpiece end of the inhaler article. The mouthpiece element may have a length in a range from about 10 mm to about 30 mm, preferably from about 15 mm to about 25 mm and more preferably from about 20 mm to about 22 mm.

A separator may be between the capsule cavity and the mouthpiece. The separator may include at least one aperture to form an air flow path from the distal air inlet through the capsule cavity, through the mouthpiece to the mouthpiece air outlet. The separator may include a plurality of apertures to form an air flow path from the distal air inlet through the capsule cavity, through the mouthpiece to the mouthpiece air outlet. The separator may define the downstream end of the capsule cavity. The separator may define the upstream end of the mouthpiece.

The capsule cavity may define a cylindrical space configured to contain a capsule (the capsule may have an obround shape or a circular cross-section, for example). The capsule cavity may have a substantially uniform or uniform diameter along the length of the capsule cavity. The capsule cavity may have a fixed cavity length. The capsule cavity has a cavity inner diameter, orthogonal to the longitudinal axis, and the capsule has a capsule outer diameter. The capsule cavity may be sized and shaped to contain an obround capsule. The capsule cavity may have a substantially cylindrical or cylindrical cross-section along the length of the capsule cavity. The capsule cavity may have a uniform inner diameter. The capsule may have an outer diameter that is about 80% to about 95% of the inner diameter of the capsule cavity. The configuration of the capsule cavity relative to the capsule may promote limited movement of the capsule during activation or piercing of the capsule.

The configuration of the capsule cavity relative to the capsule may promote the capsule to rotate with stability within the capsule cavity. The longitudinal axis of the capsule may rotate with stability co-axially with the longitudinal axis of the inhaler body during inhalation. The configuration of the capsule cavity relative to the capsule may promote the capsule to rotate with some shaking within the capsule cavity.

Stable rotation refers to the longitudinal axis of the inhaler body being substantially parallel or co-axial with the axis of rotation of the capsule. Stable rotation may refer to the absence of procession of the rotating capsule. Preferably, the longitudinal axis of the inhaler body may be substantially coextensive with the axis of rotation of the capsule. Stable rotation of the capsule may provide a uniform entrainment of a portion of nicotine particles from the capsule over two or more, or five or more, or ten or more "puffs" or inhalations by a consumer.

The distal end of the inhaler may be removable to allow for placement or replacement of capsules into the capsule cavity. The distal end of the inhaler may be configured to initiate swirling or rotational air flow though the capsule cavity. The swirling or rotational air flow though the capsule cavity causes the capsule to rotate or spin as described herein and release powder from the capsule.

The distal end of the inhaler may include an aperture to pass a needle or piercing element into the capsule cavity and form an aperture in the capsule contained therein.

The capsule distal end may be sealed with a removable sealing membrane to seal the distal end of the inhaler article. The mouthpiece endcap element seals the proximal end of the inhaler article. The user removes both the distal end sealing membrane and the mouthpiece endcap element just prior to consumption of the inhaler article.

The inhaler article may include a deformable element defining a distal end of the inhaler article. The deformable element deforms to expose an open distal end. The deformable element may define a fan fold at a distal end of the body. At least a portion of the deformable element may be formed of cellulosic material. At least a portion of the deformable element may be formed of paper. The deformable element may define at least a portion of a longitudinal sidewall of the capsule cavity. The deformable element may define a majority of the capsule cavity. The deformable element may define the upstream boundary and the sidewalls of the capsule cavity. The deformable element may extend beyond the body in a range from about 0.5 mm to about 5 mm, or from about 1 mm to about 4 mm, or about 2 mm to about 3 mm. The deformable element may be formed of paper. The deformable element may be formed of one or more paper layers. The deformable element may be formed of paper having a weight in a range of about 50 grams per square meter to about 150 grams per square meter, or from about 75 grams per square meter to about 125 grams per square meter, or from about 90 grams per square meter to about 110 grams per square meter. The deformable element may have a thickness in a range from about 50 micrometres to about 200 micrometres, or from about 100 micrometres to about 150 micrometres, or from about 110 micrometres to about 130 micrometres. Once breached or opened, the deformable element may define an opening having an open diameter that is at least about 80% or at least about 90% of the diameter of the capsule cavity. The deformable element once breached or opened may fold back onto a sidewall of the capsule cavity.

The capsule may rotate about its longitudinal or central axis when air flows through the inhaler article. The capsule may be formed of an airtight material that may be pierced or punctured by a piercing element that may be separate or combined with the inhaler. The capsule may be formed of a metallic or polymeric material that serves to keep contaminates out of the capsule but may be pierced or punctured by a piercing element prior to consumption of the nicotine particles within the capsule. The capsule may be formed of a polymer material. The polymer material may be hydroxypropyl methylcellulose (HPMC). The capsule may be a size 1 to size 4 capsule, or a size 3 capsule.

The capsule may contain pharmaceutically active particles. For instance, the pharmaceutically active particles may comprise nicotine. The pharmaceutically active particles may have a mass median aerodynamic diameter of about 5 micrometres or less, or in a range from about 0.5 micrometres to about 4 micrometres, or in a range from about 1 micrometres to about 3 micrometres.

The capsule may contain a predetermined amount of nicotine particles. The capsule may contain enough nicotine particles to provide at least 2 inhalations or "puffs", or at least about 5 inhalations or "puffs", or at least about 10 inhalations or "puffs". The capsule may contain enough nicotine particles to provide from about 5 to about 50 inhalations or "puffs", or from about 10 to about 30 inhalations or "puffs". Each inhalation or "puff" may deliver from about 0.1 mg to about 3 mg of nicotine particles to the lungs of the user or from about 0.2 mg to about 2 mg of nicotine particles to the lungs of the user or about 1 mg of nicotine particles to the lungs of the user.

The nicotine particles may have any useful concentration of nicotine based on the particular formulation employed. The nicotine particles may have at least about 1% wt nicotine up to about 30% wt nicotine, or from about 2% wt to about 25% wt nicotine, or from about 3% wt to about 20% wt nicotine, or from about 4% wt to about 15% wt nicotine, or from about 5% wt to about 13% wt nicotine. Preferably, about 50 to about 150 micrograms of nicotine may be delivered to the lungs of the user with each inhalation or "puff".

The capsule may hold or contain at least about 5 mg of nicotine particles or at least about 10 mg of nicotine particles. The capsule may hold or contain less than about 900 mg of nicotine particles, or less than about 300 mg of nicotine particles, or less than 150 mg of nicotine particles. The capsule may hold or contain from about 5 mg to about 300 mg of nicotine particles or from about 10 mg to about 200 mg of nicotine particles.

The nicotine particles may have any useful size distribution for inhalation delivery preferentially into the lungs of a user. The capsule may include particles other than the nicotine particles. The nicotine particles and the other particles may form a powder system.

The capsule may hold or contain at least about 5 mg of a dry powder (also referred to as a powder system) or at least about 10 mg of a dry powder. The capsule may hold or contain less than about 900 mg of a dry powder, or less than about 300 mg of a dry powder, or less than about 150 mg of a dry powder. The capsule may hold or contain from about 5 mg to about 300 mg of a dry powder, or from about 10 mg to about 200 mg of a dry powder, or from about 25 mg to about 100 mg of a dry powder.

The dry powder or powder system may have at least about 40%, or at least about 60%, or at least about 80%, by weight of the powder system comprised in nicotine particles having a particle size of about 5 micrometres or less, or in a range from about 1 micrometre to about 5 micrometres.

The particles comprising nicotine may have a mass median aerodynamic diameter of about 5 micrometres or less, or in a range from about 0.5 micrometres to about 4 micrometres, or in a range from about 1 micrometres to about 3 micrometres or in a range from about 1.5 micrometres to about 2.5 micrometres. The mass median aerodynamic diameter is preferably measured with a cascade impactor.

Nicotine in the powder system or nicotine particles may be a pharmaceutically acceptable free-base nicotine, or nicotine salt or nicotine salt hydrate. Useful nicotine salts or nicotine salt hydrates include nicotine pyruvate, nicotine citrate, nicotine aspartate, nicotine lactate, nicotine bitartrate, nicotine salicylate, nicotine fumarate, nicotine monopyruvate, nicotine glutamate or nicotine hydrochloride, for example. The compound combining with nicotine to form the salt or salt hydrate may be chosen based on its expected pharmacological effect.

The nicotine particles preferably include an amino acid. Preferably, the amino acid may be leucine such as L-leucine. Providing an amino acid such as L-leucine with the particles comprising nicotine, may reduce adhesion forces of the particles comprising nicotine and may reduce attraction between nicotine particles and thus reduce agglomeration of nicotine particles. The powder system described herein thus may be a free-flowing material and possess a stable relative particle size of each powder component even when the nicotine particles and optional particles are combined.

Preferably, the nicotine may be a surface modified nicotine salt where the nicotine salt particle comprises a coated or composite particle. A preferred coating or composite material may be L-leucine. One particularly useful nicotine particle may be nicotine bitartrate with L-leucine. The powder system preferably may be free flowing.

The inhaler and inhaler system may be less complex and have a simplified airflow path as compared to conventional dry powder inhalers. Advantageously, rotation of the capsule within the inhaler body aerosolizes the nicotine particles or powder system and may assist in maintaining a free-flowing powder. Thus, the inhaler article may not require the elevated inhalation rates typically utilized by conventional inhalers to deliver the nicotine particles described above deep into the lungs.

The inhaler article may use a flow rate of less than about 5 L/min or less than about 3 L/min or less than about 2 L/min or about 1.6 L/min. Preferably, the flow rate may be in a range from about 1 L/min to about 3 L/min or from about 1.5 L/min to about 2.5 L/min. Preferably, the inhalation rate or flow rate may be similar to that of Health Canada smoking regime, that is, about 1.6 L/min.

The inhaler system may be used by a consumer like smoking a conventional cigarette or vaping an electronic cigarette. Such smoking or vaping may be characterized by two steps: a first step during which a small volume containing the full amount of nicotine desired by the consumer is drawn into the mouth cavity, followed by a second step during which this small volume comprising the aerosol comprising the desired amount of nicotine is further diluted by fresh air and drawn deeper into the lungs. Both steps are controlled by the consumer. During the first inhalation step the consumer may determine the amount of nicotine to be inhaled. During the second step, the consumer may determine the volume for diluting the first volume to be drawn deeper into the lungs, maximizing the concentration of active agent delivered to the airway epithelial surface. This smoking mechanism is sometimes called "puff-inhale-exhale".

The invention is defined in the claims. However, below there is provided a non-exhaustive listing of non-limiting examples. Amy one or more of the features of these examples may be combined with any one or more features of another example, embodiment, or aspect described herein.

Example Ex1: An inhaler article includes a body extending along a longitudinal axis from a mouthpiece end to a distal end. A capsule cavity may be within the body bounded downstream by a mouthpiece. An air inlet at the distal end and an air outlet at the mouthpiece end. A separator may be between the capsule cavity and the mouthpiece including at least one aperture to form an air flow path from the capsule cavity to the mouthpiece. A first mouthpiece air channel may extend from the distal air inlet, through the capsule cavity to the mouthpiece air outlet. A second mouthpiece air channel may extend from a point downstream of the separator to the mouthpiece air outlet. The second mouthpiece air channel may be separate from the first mouthpiece air channel. A coating layer of flavour may be disposed on a surface of the second mouthpiece air channel and a protective layer may be disposed on the coating layer of flavour.

Example Ex2. The inhaler article of example Ex1, wherein the coating layer of flavour defines at least a portion of the second mouthpiece air channel.

Example Ex3. The inhaler article of any preceding example, wherein the second mouthpiece air channel has an air inlet that extends though the body of the inhaler.

Example Ex4. The inhaler article of any preceding example, wherein the second mouthpiece air channel has an air inlet that extends though the mouthpiece.

Example Ex5. The inhaler article of any preceding example, wherein the coating layer of flavour forms a gel layer.

Example Ex6. The inhaler article of any preceding example, wherein the coating layer of flavour contacts an inner diameter of the mouthpiece.

Example Ex7. The inhaler article of any preceding example, wherein the protective layer adheres to the coating layer of flavour and the protective layer defines a cylinder being coaxial with the body longitudinal axis.

Example Ex8. The inhaler article of any preceding example, wherein the protective layer comprises foil, paper, polymer, or combinations thereof.

Example Ex9. The inhaler article of any preceding example, further comprising a mouthpiece endcap sealing the mouthpiece air outlet, the mouthpiece endcap is configured to be removable from the mouthpiece element to expose the mouthpiece air outlet.

Example Ex10. The inhaler article of example Ex9, wherein the protective layer is fixed to the mouthpiece endcap and is configured to be removed from the mouthpiece element with the mouthpiece endcap.

Example Ex11. The inhaler article of example Ex10, wherein the protective layer defines a spiral configuration when removed from the mouthpiece element.

Example Ex12. The inhaler article of any one of example Ex9 to Ex11, further comprising a circumferential line of weakness forming an interface between the mouthpiece endcap and the mouthpiece end.

Example Ex13. The inhaler article of any one of example Ex9 to Ex12, wherein the mouthpiece endcap has an outer diameter equal to an outer diameter of the inhaler article body, and the mouthpiece endcap is coaxial with the inhaler article body.

Example Ex14. The inhaler article of any preceding example, further comprising a capsule disposed within the capsule cavity.

Example Ex15. The inhaler article of example Ex14, wherein the capsule contains pharmaceutically active particles comprising nicotine, the pharmaceutically active particles having a mass median aerodynamic diameter of about 5 micrometres or less, or in a range from about 0.5 micrometres to about 4 micrometres, or in a range from about 1 micrometre to about 3 micrometres.

Example Ex16. The inhaler article of any preceding example, wherein the first mouthpiece air channel being coaxial with the second mouthpiece air channel.

Example Ex17. The inhaler article of any preceding example, wherein the first mouthpiece air channel and the second mouthpiece air channel may be coaxial with the longitudinal axis of the inhaler article body.

Example Ex17. The inhaler article of any preceding example, wherein the mouthpiece may be removable and interchangeable to allow for the user to select or change the type of coating layer of flavour.

Example Ex18. The inhaler article of any preceding example wherein the body defines a narrowed portion extending to the mouthpiece end and the mouthpiece disposed about the narrowed portion, and the mouthpiece and the narrowed portion form the second mouthpiece air channel.

Example Ex19. The inhaler article of example 18 wherein the mouthpiece and the narrowed portion of the body form co-axial cylinders.

Example Ex20. The inhaler article of example 18 wherein the mouthpiece is removable from the inhaler article body and the coating layer of flavour disposed on a surface of the mouthpiece.

Example Ex21. The inhaler article of example 18 wherein the mouthpiece is removable from the inhaler article body and the coating layer of flavour disposed on an inner surface of the mouthpiece.

Example Ex22. The inhaler article of any one of example 18 to 21 wherein the mouthpiece inner surface and the narrowed portion of the body form exterior surface define an annular void space forming the second mouthpiece air channel.

Example Ex23. The inhaler article of any preceeding example, further comprising a deformable element defining a distal end of the inhaler article, the deformable element deforms to expose an open distal end.

Example Ex24. The inhaler article according to example 23, wherein the deformable element is fan folded at a distal end of the body.

The examples will now be further described with reference to the figures in which.

Figure 1:
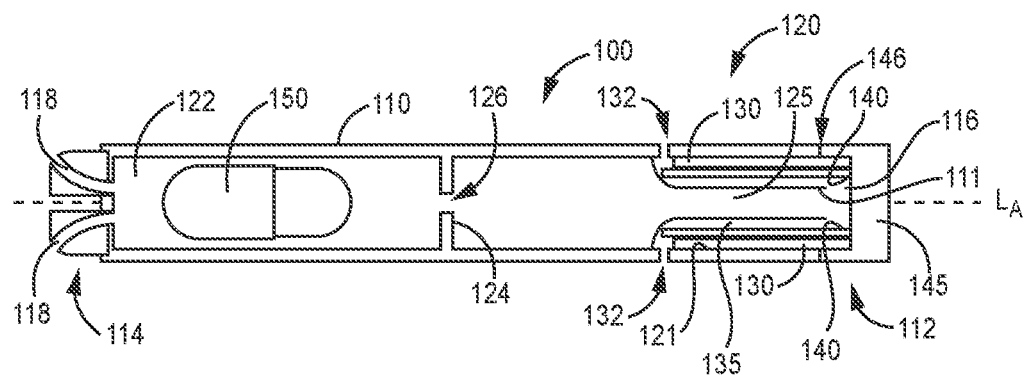
FIG. 1 is a cross-sectional schematic diagram of an illustrative inhaler article.

The schematic drawings are not necessarily to scale and are presented for purposes of illustration and not limitation. The drawings depict one or more aspects described in this disclosure. However, it will be understood that other aspects not depicted in the drawing fall within the scope and spirit of this disclosure.

Figure 2:
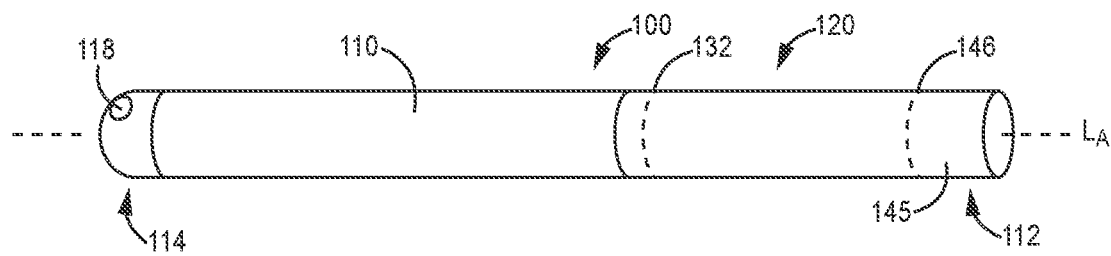
FIG. 2 is a side-elevation schematic diagram of an illustrative inhaler article.
Figure 3:
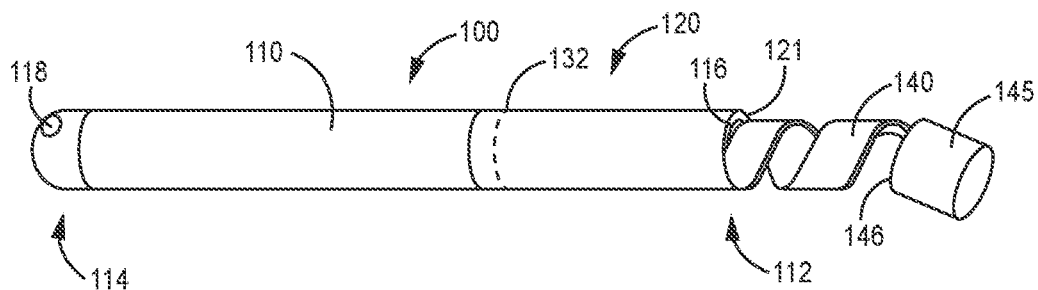
FIG. 3 is a side-elevation schematic diagram of an illustrative inhaler article where the protective layer and mouthpiece endcap is being removed.
Figure 4:
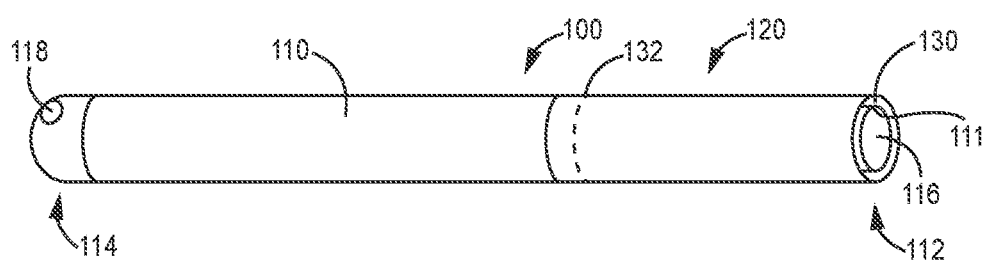
FIG. 4 is a side-elevation schematic diagram of the illustrative inhaler article of FIG. 3 where the protective layer and mouthpiece endcap is removed.
Figure 5:
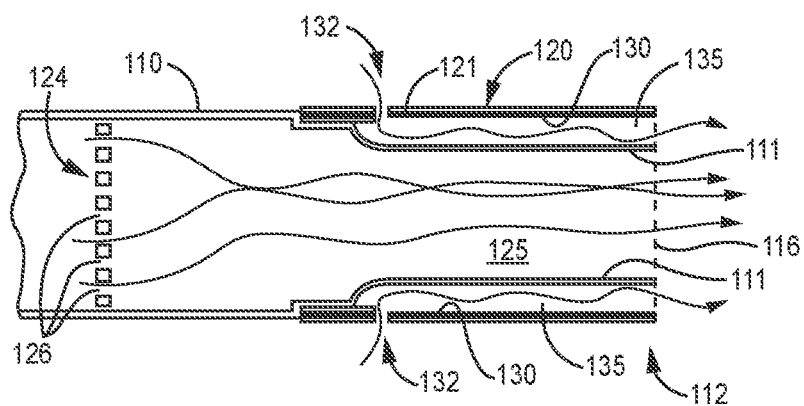
FIG. 5 is a cross-sectional schematic diagram of an exemplary mouthpiece illustrating the separate air flow paths of the first mouthpiece air channel and the second mouthpiece air channel.

FIG. 1 is a cross-sectional schematic diagram of an illustrative inhaler article 100. FIG. 2 is a side-elevation schematic diagram of an illustrative inhaler article 100. FIG. 3 is a side-elevation schematic diagram of an illustrative inhaler article 100 where the protective layer and mouthpiece endcap is being removed. FIG. 4 is a side-elevation schematic diagram of the illustrative inhaler article 100 of FIG. 3 where the protective layer and mouthpiece endcap is removed. FIG. 5 is a cross-sectional schematic diagram of an exemplary mouthpiece illustrating the separate air flow paths of the first mouthpiece air channel and the second mouthpiece air channel.

Figure 6:
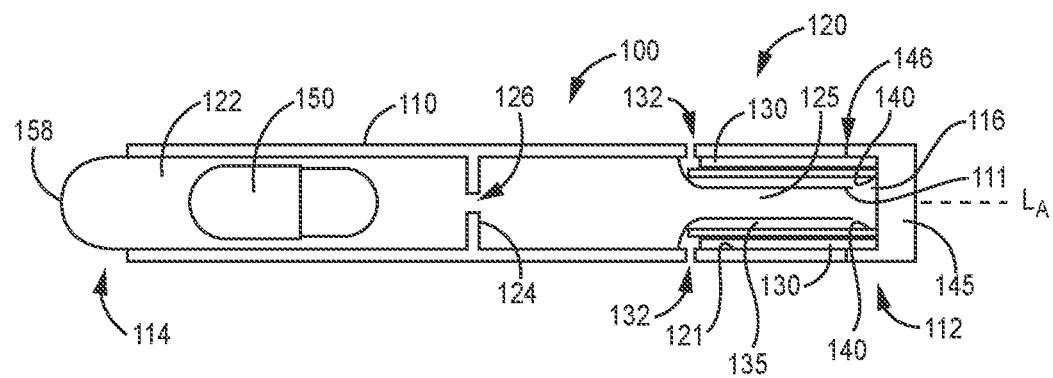
FIG. 6 is a cross-sectional schematic diagram of another illustrative inhaler article.
Figure 7:
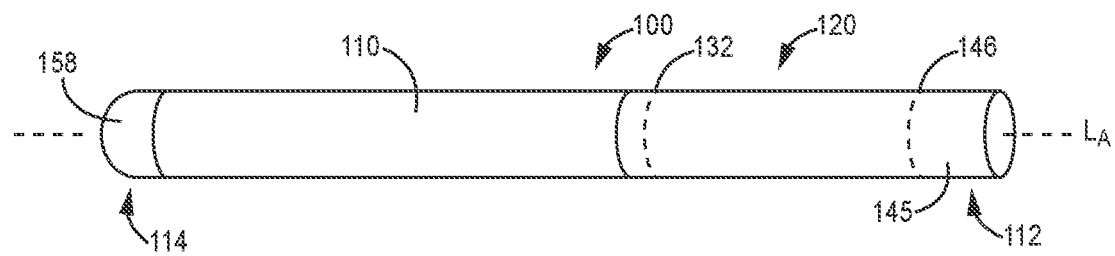
FIG. 7 is a side-elevation schematic diagram of the illustrative inhaler article of FIG. 6.
Figure 8:
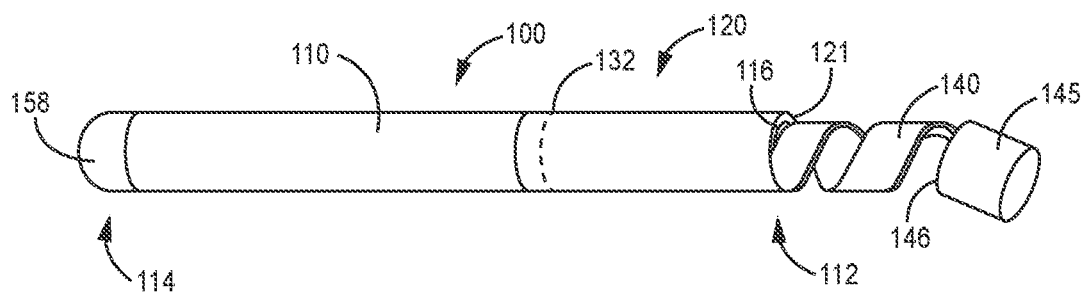
FIG. 8 is a side-elevation schematic diagram of the illustrative inhaler article of FIG. 6 where the protective layer and mouthpiece endcap is being removed.
Figures 9, 10:
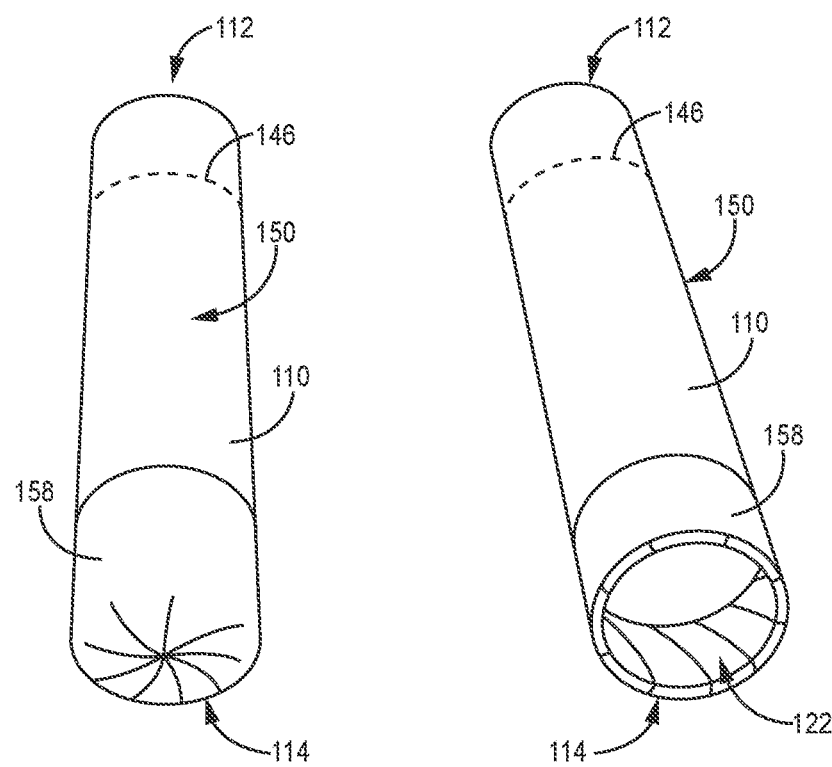
FIG. 9 is a front perspective view of the illustrative inhaler article of FIG. 6 with an intact deformable element.
FIG. 10 is a front perspective view of the illustrative inhaler article of FIG. 6 with an opened deformable element.

FIG. 6 is a cross-sectional schematic diagram of another illustrative inhaler article. FIG. 7 is a side-elevation schematic diagram of the illustrative inhaler article of FIG. 6. FIG. 8 is a side-elevation schematic diagram of the illustrative inhaler article of FIG. 6 where the protective layer and mouthpiece endcap is being removed. FIG. 9 is a front perspective view of the illustrative inhaler article of FIG. 6 with an intact deformable element 158. FIG. 10 is a front perspective view of the illustrative inhaler article of FIG. 6 with an opened deformable element 158. The inhaler article of FIG. 6 to FIG. 10 includes a deformable element 158 defining a distal end 114 of the inhaler article. The deformable element 158 deforms to expose an open distal end. The deformable element 158 is fan folded at a distal end 114 of the body 110.

An inhaler article 100 includes a body 110 extending along a longitudinal axis $L_A$ from a mouthpiece end 112 to a distal end 114. A capsule cavity 122 may be within the body 110 bounded downstream by a mouthpiece 120. An air inlet 118 at the distal end 114 and an air outlet 116 at the mouthpiece end 112. A separator 124 may be between the capsule cavity 122 and the mouthpiece 120 including at least one aperture 126 to form an air flow path from the capsule cavity 122 to the mouthpiece 120. A first mouthpiece air channel 125 may extend from the distal air inlet 118, through the capsule cavity 122 to the mouthpiece air outlet 116. A second mouthpiece air channel 135 may extend from a point downstream of the separator 124 to the mouthpiece air outlet 116. The second mouthpiece air channel 135 may be separate from the first mouthpiece air channel 125. A coating layer of flavour 130 may be disposed on a surface of the second mouthpiece air channel 135 and a protective layer 140 may be disposed on the coating layer of flavour 130.

The second mouthpiece air channel 135 has an air inlet 132 that extends though the body 110 of the inhaler 100. The second mouthpiece air channel 135 has an air inlet 132 that may extend though the mouthpiece 120. The second mouthpiece air channel 135 has an air inlet 132 that may extend through the sidewall of the mouthpiece 120. The second mouthpiece air channel 135 air inlet 132 may be formed of a plurality of holes or apertures located circumferentially about the mouthpiece 120.

The first mouthpiece air channel 125 may be coaxial with the second mouthpiece air channel 135. the first mouthpiece air channel 125 and the second mouthpiece air channel 135 may be coaxial with the longitudinal axis $L_A$ of the inhaler article body 110. The first mouthpiece air channel 125 may be coaxial and parallel with the second mouthpiece air channel 135.

The second mouthpiece air channel 135 may be formed by disposing the mouthpiece 120 about a reduced diameter portion 111 of the inhaler body 110. The shaped, educed diameter, or narrowed portion 111 of the body may extend along the mouthpiece region to the mouthpiece end 112 of the inhaler article 100. The mouthpiece 120 may fit over the reduced diameter portion 111 of the inhaler body 110 to form the second mouthpiece air channel 135.

The second mouthpiece air channel 135 may define an annular void space between the mouthpiece inner surface 121 and the external surface of the reduced diameter portion 111 of the inhaler body 110. The coating layer of flavour 130 may contact an inner diameter surface 121 of the mouthpiece 120.

The mouthpiece 120 may be a replaceable element on the inhaler body 100. Thus a user may remove a mouthpiece 120 having a depleted coating layer of flavour 130 and place a different or refreshed mouthpiece 120 over the reduced diameter portion 111 and onto the inhaler body 110.

The protective layer 140 may adhere to the coating layer of flavour 130 and the protective layer 140 may defines a cylinder being coaxial with the body 110 longitudinal axis $L_A$. A mouthpiece endcap 145 may seal the mouthpiece air outlet 116, the mouthpiece endcap 145 may be configured to be removable from the mouthpiece 120 to expose the mouthpiece air outlet 116. The protective layer 140 may be fixed to the mouthpiece endcap 145 and configured to be removed from the mouthpiece 120 with the mouthpiece endcap 145. The protective layer 140 may defines a spiral configuration when removed from the mouthpiece 120, as illustrated in FIG. 3.

The protective layer 140 may seal the air inlet 132 of the second mouthpiece air channel 135. The protective layer 140 may extend from the mouthpiece endcap 145 along the coating layer of flavour 130 and over the air inlet 132 of the second mouthpiece air channel 135 to provide a barrier and reduce or prevent migration of the flavour material of the coating layer of flavour 130.

A circumferential line of weakness 146 forms an interface between the mouthpiece endcap 145 and the mouthpiece end 112. A user may separate the mouthpiece endcap 145 from the mouthpiece 120 at the circumferential line of weakness 146.

A capsule 150 may be disposed within the capsule cavity 122. The capsule 150 may be replaceable by removing the distal end 114 of the inhaler article 100 or the mouthpiece 120 and removing or inserting a capsule 150. The distal end 114 air inlet 118 may initiate rotational or swirling airflow into the capsule cavity to rotate or spin the capsule 150 and release dry powder particles into the airflow.

As illustrated in FIG. 5, airflow from the capsule cavity containing entrained dry powder particles pass through the separator and out the mouthpiece air outlet 116 along the first air channel 125. A separate air flow passes through the body 110 of the inhaler into the second air channel 135 where flavour volatizes into that airflow and out the mouthpiece air outlet 116 along the second air channel 135. The second air channel 135 may provide a flavour ventilation airflow that is separate and isolated from the airflow from the capsule cavity containing entrained dry powder particles that pass through the first airflow channel 125. Thus, dry powder particles and flavour do not contact each other within the inhaler article 100. Dry powder particles and flavour contact each other only once they have exited the inhaler article 100. Airflow along the first airflow channel 125 may be parallel and coaxial with the separate airflow along the second air channel 135. Airflows from the first airflow channel 125 and the second air channel 135 may combine once they exit the inhaler article 100.

For the purpose of the present description and of the appended claims, except where otherwise indicated, all numbers expressing amounts, quantities, percentages, and so forth, are to be understood as being modified in all instances by the term "about". Also, all ranges include the maximum and minimum points disclosed and include any intermediate ranges therein, which may or may not be specifically enumerated herein. In this context, therefore, a number A is understood as A±2% of A. Within this context, a number A may be considered to include numerical values that are within general standard error for the measurement of the property that the number A modifies. The number A, in some instances as used in the appended claims, may deviate by the percentages enumerated above provided that the amount by which A deviates does not materially affect the basic and novel characteristic(s) of the claimed invention. Also, all ranges include the maximum and minimum points disclosed and include any intermediate ranges therein, which may or may not be specifically enumerated herein.

The invention claimed is:

1. An inhaler article comprising:
 a body extending along a longitudinal axis from a mouthpiece end to a distal end;
 a capsule cavity within the body bounded downstream by a mouthpiece;
 an air inlet at the distal end;
 an air outlet at the mouthpiece end;
 a separator between the capsule cavity and the mouthpiece comprising at least one aperture to form an air flow path from the capsule cavity to the mouthpiece;
 a first mouthpiece air channel extending from the distal air inlet, through the capsule cavity to the mouthpiece air outlet;
 a second mouthpiece air channel extending from a point downstream of the separator to the mouthpiece air outlet, the second mouthpiece air channel being separate from the first mouthpiece air channel; and
 a coating layer of flavour disposed on a surface of the second mouthpiece air channel and a protective layer disposed on the coating layer of flavour.

2. The inhaler article of claim 1, wherein the coating layer of flavour defines at least a portion of the second mouthpiece air channel.

3. The inhaler article of claim 1, wherein the second mouthpiece air channel has an air inlet that extends though the body of the inhaler.

4. The inhaler article of claim 1, wherein the second mouthpiece air channel has an air inlet that extends though the mouthpiece.

5. The inhaler article of claim 1, wherein the coating layer of flavour forms a gel layer.

6. The inhaler article of claim 1, wherein the body defines a narrowed portion extending to the mouthpiece end and the mouthpiece disposed about the narrowed portion, and the mouthpiece and the narrowed portion form the second mouthpiece air channel.

7. The inhaler article of claim 6, wherein the mouthpiece is removable from the inhaler article body and the coating layer of flavour disposed on an inner surface of the mouthpiece.

8. The inhaler article of claim 1, wherein the protective layer adheres to the coating layer of flavour and the protective layer defines a cylinder being coaxial with the body longitudinal axis.

9. The inhaler article of claim 1, wherein the protective layer comprises foil, paper, polymer, or combinations thereof.

10. The inhaler article of claim 1, further comprising a mouthpiece endcap sealing the mouthpiece air outlet, the mouthpiece endcap is configured to be removable from the mouthpiece end to expose the mouthpiece air outlet and the protective layer is fixed to the mouthpiece endcap and configured to be removed from the mouthpiece end with the mouthpiece endcap.

11. The inhaler article of claim 10, wherein the protective layer defines a spiral configuration when removed from the mouthpiece end.

12. The inhaler article of claim 10, further comprising a circumferential line of weakness forming an interface between the mouthpiece endcap and the mouthpiece end.

13. The inhaler article of claim 10, wherein the mouthpiece endcap has an outer diameter equal to an outer diameter of the inhaler article body, and the mouthpiece endcap is coaxial with the inhaler article body.

14. The inhaler article of claim 1, further comprising a capsule disposed within the capsule cavity.

15. The inhaler article of claim 14, wherein the capsule contains pharmaceutically active particles comprising nicotine, the pharmaceutically active particles having a mass median aerodynamic diameter of in a range from about 0.5 micrometres to about 4 micrometres.

16. The inhaler article of claim 1, further comprising a deformable element defining a distal end of the inhaler article, the deformable element deforms to expose an open distal end.

17. The inhaler article according to claim 16, wherein the deformable element is fan folded at a distal end of the body.

18. The inhaler article of claim 5, wherein the protective layer adheres to the coating layer of flavour and the protective layer defines a cylinder being coaxial with the body longitudinal axis.

19. The inhaler article of claim 8, wherein the protective layer comprises foil, paper, polymer, or combinations thereof.

20. The inhaler article of claim 11, further comprising a circumferential line of weakness forming an interface between the mouthpiece endcap and the mouthpiece end.

* * * * *